US007094593B1

(12) United States Patent
Pausch et al.

(10) Patent No.: US 7,094,593 B1
(45) Date of Patent: Aug. 22, 2006

(54) METHOD FOR IMPROVING THE FUNCTION OF HETEROLOGOUS G PROTEIN-COUPLED RECEPTORS

(75) Inventors: Mark Henry Pausch, Rocky Hill, NJ (US); Jurgen Wess, Bethesda, MD (US)

(73) Assignees: BASF Aktiengesellschaft, (DE); The United States of America as represented by the Department of Health, Washington, DC (US)

( * ) Notice: Subject to any disclaimer, the term of this patent is extended or adjusted under 35 U.S.C. 154(b) by 0 days.

(21) Appl. No.: 09/786,033

(22) PCT Filed: Sep. 1, 1999

(86) PCT No.: PCT/US99/20013

§ 371 (c)(1),
(2), (4) Date: Jul. 3, 2001

(87) PCT Pub. No.: WO00/12705

PCT Pub. Date: Mar. 9, 2000

Related U.S. Application Data (60) Provisional application No. 60/098,704, filed on Sep. 1, 1998.

(51) Int. Cl.
*C12N 1/15* (2006.01)
*G01N 33/569* (2006.01)
*G01N 33/566* (2006.01)

(52) U.S. Cl. .......................... 435/254.11; 435/7.31; 435/69.7; 435/69.5; 435/254.2; 435/254.21; 435/320.1; 436/501; 536/23.5; 530/350

(58) Field of Classification Search .............. 435/7.21, 435/6, 69.1, 252.3, 320.1; 436/501; 536/23.5; 530/350, 300; 514/2
See application file for complete search history.

(56) References Cited

U.S. PATENT DOCUMENTS 5,576,210 A * 11/1996 Sledziewski
5,789,184 A *  8/1998 Fowlkes

FOREIGN PATENT DOCUMENTS

| WO | WO95/21925 | 8/1995 |
| WO | WO96/00739 | 1/1996 |
| WO | WO 96/00739 | * 1/1996 |
| WO | WO 92/05244 | * 4/1996 |
| WO | WO 98/38217 | 9/1998 |
| WO | WO00/22131 | 4/2000 |

OTHER PUBLICATIONS

Bonner et al., Science 237(527-537)1987.*
Feng-y et al., Molecular and Cellular Biology, 20(5)563-574)2000.*
Eggerickx, D., et al., "Molecular Cloning of an Orphan G-Protein-Coupled Receptor that Constitutively Activates Adenylate Cyclase", *Biochemical J.* 309:837-843, 1995.
Kjelsberg, M.A., et al., "Constitutive Activation of the Alpha 1B-Adrenergic Receptor by all Amino Acid Substitutions at a Single Site", *J. Biol. Chem.* 267(3):1430-1433, Jan. 1992.
Pauwels, P.J. and T. Wurch, "Review: Amino Acid Domains Involved in Constitutive Activation of G-Protein-Coupled Receptors", *Mol. Neurobiol.* 17(1-3):109-135, 1998.
Samama, P., et al., "A Mutation-Induced Activated State of the Beta2-Adrenergic Receptor", *J. Biol. Chem.* 268(7):4625-4636, Mar. 1993.
M.H. Pausch et al., "G-Protein-Coupled receptors in *Saccharomyces cerevisiae*:high-throughput screening assays for drug discovery", *Trends in Biotechnology*, vol. 15, No. 12, pp. 487-494, (Dec. 1997).
O. Moro, et al., "Serine-and Threonine-rich Domain regulates internaliz ation of muscarinic cholinergic Receptors", *Jo urnal of Biological Chemistry*, vol. 268, No. 10, pp. 6862-6865 (Apr. 1993).
K. Blueml, et al., "Functional Role of A Cytoplasmic Aromatic Amino Acid In Muscarinic Receptor-Mediated Activ ation of Phospholipase C", *Jo urnal of Biological Chemistry*, vol. 269, No. 15, pp. 11537-11541, (Apr. 1994).
J. Wess, et al., "Identification of a small intracelular region of the mascarinic m3 receptor as a determinant of selective coupling to PI turnov er", *FEBS Letters*, vol. 258, No. 1, (Nov. 1989).
J. Wess, et al., "G protein-coupled receptors: m olecular mechanisms involved in receptor activation and selectiv ity of G-protein recognition" *FASEB Jo urnal, US, Fed. of American Soc. for Experimental Biology*, vol. 11, No. 5, pp. 346-354, (Apr. 1997).
M.H. Pausch, etal., "Heterologous G Protein-Coupled Receptors Ex pressed in *Saccharom yces cerevisiae*: Methods for Genetic Analy sis and Ligand Identif ication", *Identification and Expression of G-Protein-Coupled Receptors*, pp. 196-212 (May 1999).
A. Scheer, et al., "Constitutiv ely Active G Protein-Coupled Receptors: Potential M echanisms of Receptor Activ ation" *Journal of Receptor and Signal Transduction Research*, vol. 17, No. 1-3, pp. 57-73, (1997).

* cited by examiner

*Primary Examiner*—Elizabeth Kemmerer
*Assistant Examiner*—Michael Brannock
(74) *Attorney, Agent, or Firm*—Finnegan, Henderson, Farabow, Garrett & Dunner, LLP

(57) ABSTRACT

This invention relates to mutant G protein-coupled receptors with improved G-protein coupling and receptor response, yeast cells expressing such receptors, vectors useful for making such cells, and methods of making and using same.

11 Claims, 5 Drawing Sheets

SEQUENCE LISTING

```
<160> NUMBER OF SEQ ID NOS: 30

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
aaaagatcta aatgtaccc ctacgacgtc ccc                              33

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
aaactcgagc tacaaggcct gctccggcac tcgc                            34

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
atagtcatga tggtgaccgg tatgtaaaag gcagcgatc                       39

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      oligonucleotide
```

```
<400> SEQUENCE: 4
gccttcatca tcacgtggac cccctacacc                                      30

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
cgatcgctgc cttttactta ccggtcacca tcatgactat                           40

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
gttgtagggg gtccacgtga tgatgaaggc                                      30

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
aaaagatcta aaatgtacgg aaaccagacg aac                                  33

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
ccagtagagg aagcacatga tggtcaggcc taagtagaag gcggccagtg c              51

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ttcatcatca cgtggactcc gtacaacatc                                      30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
```

```
aaactcgagt tatctaattg tagacgcggc                                    30

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
acttagatca aaaaatggag cgctcaagct gaaccg                             36

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
tcccgtcgac tcagccaggc cccagtgtgc tg                                 32

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
cgagggccag ggactggccc cggccgggcc cggctttggg tctcg                   45

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
cgagacccaa agccgggccc ggccggggcc agtccctggc cctcg                   45

<210> SEQ ID NO 15
<211> LENGTH: 8
<212> TYPE: PRT
<213> ORGANISM: Rattus sp.

<400> SEQUENCE: 15

Gln Trp Val Gln Ala Pro Ala Cys
 1               5

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
aaaaagatct aaaatggcca ctgttaccta t                                  31
```

```
<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
ctcagagcgg cgtcgccgct gacacgaggg cgcccg                              36

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
gcgccctcgt gtcagcggcg acgccgctct gag                                 33

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
aaaactcgag ttacagatgg ctcagtgtgc t                                   31

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
ggccaggatc caaaaatggg ctccctgcag ccggacgc                            38

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
cgggccccgc gggcgctcgg ggcccagacc gttgggc                             37

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
cgggcgacag cctgccgcgg c                                              21
```

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
agcggtcgac tcacacgatc cgcttcctgt cccc                               34

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
agtcagatct aagcttaaaa atgcacctca acagctcc                           38

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
agtcagatct ctagtacagg gtctccc                                       27

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
agagagatct ttagcgccac ccaggacaaa ggc                                33

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
aaaagatcta aaatgatcga cgagacgctt c                                  31

<210> SEQ ID NO 28
<211> LENGTH: 111
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
ccgcttggtg atctgacttc tggtttctgt cccagaggcc tgtaggccag ccagctcttt   60
ggtacgcttc tcagtttcct tatagatctt ccagtacacg caaattattg c            111

```
<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
aaaactcgag tcaataatcg tgaataaggc a                                    31

<210> SEQ ID NO 30
<211> LENGTH: 110
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
ggcctacagg cctctgggac agaaaccaga agtcagatca ccaagcggaa gaggatgtcg     60
ctcatcaagg agaagaaggc cgccagaacg ctagcaatta ttacaggtac                110
```

METHOD FOR IMPROVING THE FUNCTION OF HETEROLOGOUS G PROTEIN-COUPLED RECEPTORS

STATEMENT OF RELATED APPLICATIONS

This application hereby claims the benefit of U.S. provisional application Ser. No. 60/098,704 filed Sep. 1, 1998. The entire disclosure of this provisional application is relied upon and incorporated by reference herein.

FIELD OF THE INVENTION

This invention relates to mutant G protein-coupled receptors with improved G-protein coupling and receptor response, host cells expressing such receptors, vectors useful for making such cells, and methods of making and using same.

BACKGROUND OF THE INVENTION

The actions of many extracellular signals, such as neurotransmitters, hormones, odorants, and light, are mediated by a triad of proteins which has been identified in organisms from yeast to mammals. This triad consists of a receptor, coupled to a trimeric guanine nucleotide-binding regulatory protein (G protein), which in turn is coupled to a cellular effector. These receptors have seven transmembrane domains and are named for their association with the G protein as "G protein-coupled receptors" ("GPCRs").

The regulatory G proteins are comprised of three subunits: a guanylnucleotide binding $\alpha$ subunit; a $\beta$ subunit; and a $\gamma$ subunit. B. R. Conklin and H. R. Bourne (1993). G proteins cycle between two forms, depending on whether GDP or GTP is bound to the $\alpha$ subunit. When GDP is bound, the G protein exists as a heterotrimer, the G$\alpha\beta\gamma$ complex. When GTP is bound, the a subunit dissociates, leaving a G$\beta\gamma$ complex. Importantly, when a G$\alpha\beta\gamma$ complex operatively associates with an activated G protein coupled receptor in a cell membrane, the rate of exchange of GTP for bound GDP is increased and, hence, the rate of disassociation of the bound G$\alpha$ subunit from the G$\beta\gamma$ complex increases. The free G$\alpha$ subunit and G$\beta\gamma$ complex are capable of transmitting a signal to downstream elements of a variety of signal transduction pathways. Examples of these downstream cellular effector proteins include, among others, adenylate cyclases, ion channels, and phospholipases. This fundamental scheme of events forms the basis for a multiplicity of different cell signaling phenomena. H. G. Dohlman et al. (1991).

Because of their ubiquitous nature in important biochemical pathways, the G protein-coupled receptors represent important targets for new therapeutic drugs. In turn, the discovery of such drugs will necessarily require screening assays of high specificity and throughput termed high-throughput screening (HTS) assays. Screening assays utilizing microorganisms, such as yeast strains, genetically modified to accommodate functional expression of the G protein-coupled receptors offer significant advantages in research involving ligand binding to numerous receptors implicated in various disease states.

However, microorganisms transformed with wild-type receptors may perform poorly in growth assays, exhibiting, for example, the inability to interact with the heterotrimeric G protein, inappropriate localization and/or desensitization. Many GPCRs are phosphorylated in response to chronic and persistent agonist stimulation which often leads to desensitization followed by sequestration or internalization of the receptors. Desensitization of GPCRs causes uncoupling from interaction with heterotrimeric G proteins. This process is mediated by a variety of regulatory receptor protein kinases, including G protein-coupled receptor kinases (GRK), protein kinase A (PKA), protein kinase C (PKC), and casein kinases (CK). Internalization involves removal of GPCRs from the plasma membrane via receptor-mediated endocytosis. Internalized receptors may be recycled back to the cell surface, or delivered to a lysosomal/vacuolar compartment for degradation. The ubiquitin-mediated degradative pathway is also involved in this process. The ultimate result of receptor phosphorylation and sequestration/internalization is often cell growth arrest, which significantly reduces the utility of the genetically modified microorganism in screening assays.

SUMMARY OF THE INVENTION

It is an object of this invention to provide modified G protein-coupled receptors that function well in high throughput screening assays, implemented in any eukaryotic cell, preferably yeast cells. Thus, a first aspect of the present invention is directed to nucleotide sequences encoding a G protein-coupled receptor which has been modified to improve the function of the GPCR by causing the receptor to couple more efficiently with the heterotrimeric G protein and/or to fail to interact with the cell desensitization and/or sequestration/internalization machinery, and/or to appropriately localize to the plasma membrane. In preferred embodiments, such modifications lead to improved agonist-stimulated growth-promoting ability. One specific modification of the nucleotide sequence encoding a G protein-coupled receptor encompassed by this invention is a mutation in any intracellular domain or membrane region proximal to internal domains. The mutation may be a deletion, including, for example, a point mutation.

This invention is also directed to chimeric GPCRs in which intracellular domains of heterologous GPCRs that provide favorable G protein coupling properties or domains not subject to the yeast cell desensitization and/or sequestration/internalization machinery are used to replace comparable domains in GPCRs of interest. This invention also relates to the modified nucleotide sequences encoding the chimeric GPCRs, to expression vectors comprising the modified nucleotide sequences, and to host cells transformed therewith.

An additional aspect of this invention is an improved method of assaying compounds to determine effects of ligand binding to the mutant or chimeric GPCRs of this invention by measuring the effect of the test compound on cell growth. The mutant GPCRs prevent or reduce the rate of cell growth arrest due to chronic and persistent agonist stimulation, thereby decreasing the number of false negatives that occur with prior art screening methods and/or increasing the sensitivity of the bioassay.

BRIEF DESCRIPTION OF THE DRAWINGS

FIG. 3 depicts the results of an agar-based plate bioassay.

FIG. 4 depicts yeast cells transformed with rSSTR3 and with rSSTR3ΔIC3.

DETAILED DESCRIPTION OF THE INVENTION

Modified G Protein-Coupled Receptors

Nucleotide sequences encoding G protein-coupled receptors may be modified to improve the function of the GPCR by causing the receptor to couple more efficiently with the heterotrimeric G protein and/or to fail to interact with the cell desensitization and/or sequestration/internalization machinery. Such modifications lead to improved agonist-stimulated yeast cell growth-promoting ability. The improvement of GPCR-G protein coupling and/or elimination of receptor phosphorylation and/or sequestration/internalization in the host cell provides a means to improve the function of wildtype heterologous GPCRs that fail to stimulate a useful yeast cell growth response. Thus, GPCRs that fail to function in their wild type form may be made to work by the methods of this invention.

The improvement of GPCR-G protein coupling and or elimination of receptor phosporylation and/or sequestration/internalization in the host cell may be assessed by using routine techniques, such as those described in the Examples set fort below or known to those of skill in the art. For example, improvement of the function of a mutated GPCR over wild type may be quantified as an increase in the signal-to-noise ratio and/or in the sensitivity of the liquid bioassay. The signal-to-noise ratio is determined by comparing the agonist-induced growth rate to the growth rate observed in the absence of agonist. A statistically-significant increase in the signal-to-noise ratio resulting from agonist-stimulation of a mutated GPCR over similar values obtained from cells containing a wild type receptor indicates that the function of the mutated GPCR has been improved.

The sensitivity of the liquid bioassay is defined as the agonist concentration necessary to produce a half-maximal growth rate (ED50 or EC50). The sensitivity of the bioassay is increased if a mutated GPCR produces a half-maximal growth rate at an agonist concentration that is less than that required by the wild type GPCR.

Similarly, the more qualitative agar based bioassay will reflect increases in signal-to-noise ratio and/or sensitivity due to agonist stimulation of mutated GPCRs. In the agar based bioassay, signal-to-noise ratio increases are determined by comparing the extent of growth within the agonist induced growth zone resulting from stimulation of mutated and wild type receptor. The sensitivity of the bioassay is proportional to the radius of the growth zone. Since applied compounds diffuse radially from the site of application to the agar, agonist concentration varies with the square of the radius of the growth zone. Thus, a larger zone of growth in response to agonist activation of mutated GPCRs reflects an increase in sensitivity.

Any G protein-coupled receptor may be employed in practicing this invention. Examples of such receptors include, but are not limited to, adenosine receptors, somatostatin receptors, dopamine receptors, cholecystokinin receptors, muscarinic cholinergic receptors, α-adrenergic receptors, β-adrenergic receptors, opiate receptors, cannabinoid receptors, growth hormone releasing factor, glucagon, serotonin receptors, vasopressin receptors, melanocortin receptors, and neurotensin receptors. In certain preferred embodiments, the receptor is a muscarinic acetylcholine receptor and more preferably, the muscarinic acetylcholine receptor is of the M3 subtype.

Similarly, any suitable host cell may be transformed with the nucleotide sequences encoding the modified G protein-coupled receptors of this invention. Examples of suitable host cells are yeast cells, mammalian cells, insect cells, and bacterial cells. Preferably, the host cells are yeast cells.

One generalizable method for improving the function of a GPCR expressed in a host cell is by modification or elimination of intracellular domains of the GPCR, such as the third intracellular loop (IC3) sequences of the G protein-coupled receptor. Because the desensitization and internalization machinery acts upon the intracellular domains of the GPCR, elimination of the intracellular domains of the GPCRs produces a more stable receptor expression. This has been demonstrated in experiments conducted in mammalian cells. Muscarinic acetylcholine receptors, including the M3 subtype, lacking a domain of their third intracellular loop thought to be involved in receptor internalization, are maintained in the plasma membrane to a greater extent than their wild type counterparts. Moro et al. (1993).

Representative embodiments of the invention are described in more detail in the following examples.

EXAMPLE 1

Functional Expression of a Mutated Rat M3 Muscarinic Acetylcholine Receptor (MAR) in Yeast The third intracellular loops of GPCRs are thought to interact with and participate in the activation of G proteins upon agonist binding. J. Wess (1997). Mutations in IC3 of the yeast mating pheromone receptors, Ste2 and Ste3 have profound effects on coupling the G proteins. C. Boone et al. (1993) and C. Clark et al. (1994). Importantly, deletion of portion of the IC3 of mammalian MARs, in particular the rat M3 MAR, is correlated with improved functional expression in mammalian cells with retention of full ability to couple to the heterotrimeric G protein, Gq (Gαβγ). The mutated M3 MAR retains all external loops. Transmembrane domains (TMDs) and internal domains other than the IC3 are unchanged. The IC3, found between $5^{th}$ and $6^{th}$ membrane spanning helices, was the only domain modified. The bulk of this domain, 196 amino acids in the center of the IC3 (Ala273-Lys469), were deleted, leaving only 22 amino acids proximal to both the $5^{th}$ and $6^{th}$ transmembrane helices. Thus, the third intracellular loop of the MAR containing the IC3 deletion (IC3Δ) is 44 amino acids in length, compared to 240 amino acids in the IC3 of wild type M3 MAR. The improvement in functional expression may due to elimination of domains known to interact with cellular desensitization mechanisms, allowing more functional MAR to be retained at the cell surface.

In order to test the possibility that this IC3Δ mutation would also improve functional expression in yeast, the DNA sequences encoding the wild type and IC3Δ rat M3 MARs were cloned into proximity to the glycerol-phosphate dehydrogenase promoter in the yeast expression plasmid, p426GPD, by standard methods. Rat M3 MAR sequences were amplified by PCR using oligonucleotides containing 5' BglII (AAAAGATCT AAA ATG TAC CCC TAC GAC GTC CCC) (SEQ ID NO: 1) and 3' XhoI (AAA CTCGAG CTA CAA GGC CTG CTC CGG CAC TCG C) (SEQ ID NO: 2) sites. The resulting PCR product was digested with the appropriate restriction endonucleases, purified and ligated into appropriate sites in p426GPD. To form the rat M3 IC3Δ, three M3 MAR fragments were amplified by PCR. An amino-terminal coding fragment was amplified using oligonucleotides containing 5' BglII (AAAAGATCT AAA ATG TAC CCC TAC GAC GTC CCC) (SEQ ID NO: 1) and 3' AgeI (ATAGTCATGATGGTG ACCGGT ATGTAAAAG-GCAGCGATC) (SEQ ID NO: 3) sites. A carboxy-terminal coding fragment was amplified using oligonucleotides containing 5' PmlI (GCCTTCATCAT CACGTG GAC-CCCTACACC) (SEQ ID NO: 4) and 3' XhoI (AAA CTCGAG CTA CAA GGC CTG CTC CGG CAC TCG C) (SEQ ID NO: 2) sites. An IC3 coding fragment was amplified using oligonucleotides containing 5' AgeI (CGATCGCTGCCTTTTACTT ACCGGT CACCATCAT-GACTAT) (SEQ ID NO: 5) and 3' PmlI (GTTG-TAGGGGGTC CACGTG ATGATGAAGGC) (SEQ ID NO: 6) sites using the M3 IC3Δ sequence. J. Wess (1997). The resulting PCR products were digested with the appropriate restriction endonucleases, purified and ligated into appropriate sites in p426GPD. Plasmids were confirmed by restriction endonuclease mapping and DNA sequencing. Using a conventional lithium acetate transformation procedure, the resulting plasmids were introduced into yeast cells useful for performing assays of GPCR agonist-stimulated growth, such as those described in U.S. Pat. No. 5,691,188, incorporated herein by reference, including, specifically, the MPY578fc cells described in Pausch et al. (1998).

Figure 1A:
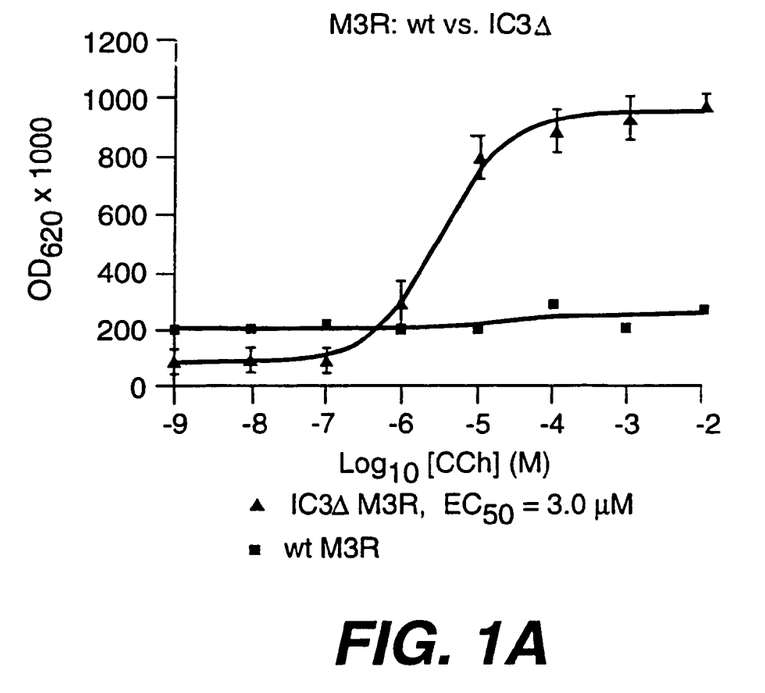
FIG. 1A depicts the results of liquid culture assays on yeast cells containing the rat M3 muscarinic acetylcholine receptor (MAR) using MAR agonist carbachol (CCh). Yeast cells containing a M3 MAR with a deletion in the third intracellular loop (IC3Δ) produced an agonist-dependent growth response, while the wild type MAR did not, indicating that the M3 MAR IC3Δ is functional GPCR.

Yeast cells containing the MARs were assayed in liquid culture using the MAR agonist carbachol (CCh). The cells were cultured overnight in 2 ml SC-glucose-ura medium. The cells were diluted 500 fold in SC-glucose-ura-his, pH 6.8 medium containing 5 mM 3-aminotriazole to decrease basal growth rate. Samples of the cell suspension (180 μl) were dispensed to wells of sterile 96 well microtiter dishes containing 20 μl of serially-diluted samples ($10^{-1}$–$10^{-8}$ M) of the muscarinic receptor agonists. The plates were incubated at 30° C. for 18 hours with agitation (600 rpm). Growth was monitored by recording increases in $OD_{620}$ using a microplate reader. Assays were conducted in duplicate and growth rate measurements obtained during the logarithmic phase of yeast cell growth. Optical density measurements were analyzed using GraphPad Prism and are presented as the mean±SEM and were plotted vs. agonist concentration. As shown in FIG. 1, the yeast cells containing the M3 MAR IC3Δ produced an agonist-dependent growth response, demonstrating that the M3 MAR IC3Δ is functional, while the wild type MAR is non-functional, as indicated by the lack of agonist-dependent yeast cell growth. The growth response of the M3 MAR IC3Δ containing cells was dose-dependent giving an $EC_{50}$ for carbachol (CCh) equal to 3 μM. This value matches the $K_D$ for CCh obtained in HEK cells (7.9 μM) and the $EC_{50}$ for CCh induced $IP_3$ (inositol triphosphate) accumulation (4.0 μM), suggesting that the M3 MAR IC3Δ retains the expected pharmacological properties when expressed in yeast cell membranes. Further, the growth response is blocked by the MAR-specific antagonist, atropine (At).

Alternatively, the response to CCh by yeast cells containing the M3 MAR IC3Δ may be observed by measuring the agonist-induced increase in fluorescent emission from a green fluorescent protein reporter gene whose expression is stimulated by MAR agonists. Green fluorescent protein (GFP) is a protein from Aequorea that is intrinsically fluorescent when expressed in yeast cells. The fluorescence from GFP is detectable in live yeast calls, making it possible to measure the level of its expression without any deleterious treatment of the yeast cells. This feature is particularly advantageous in the reporter gene assays that do not require additional steps to permit its detection. An inducible reporter gene that is useful in detecting the agonist-activation of heterologous GPCRs expressed in yeast utilizes transcriptional promoters that are activated by the mating signal transduction pathway. One such promoter is the FUS2 promoter. In the absence of agonist stimulation, little or no expression of the Fus2 protein or any other protein whose expression is directed by the FUS2 promoter is detectable. After treatment with agonist, transcription from the FUS2 promoter is induced up to 700 fold, leading to substantial increases in Fus2 expression or in the expression of any gene product whose expression is placed under control of the FUS2 promoter. Thus, yeast cell fluorescence resulting from GFP expression under the control of the FUS2 promoter from a FUS2-GFP reporter gene is only observed after agonist activation of a heterologous GPCR.

In order to produce a GFP reporter gene, DNA sequences encoding the enhanced GFP (EGFP, Clonetech), FUS2 promoter and FUS2 transcriptional terminator sequences were amplified by PCR. The fragments were assembled into the centromere containing plasmid pRS414 so as to place EGFP expression under control of the pheromone responsive FUS2 promoter in the centromere containing plasmid pRS414, producing plasmid pMP241. Using a conventional lithium acetate transformation procedure, the resulting plasmids were introduced into yeast cells of the kind described in U.S. Pat. No. 5,691,188, that are useful for performing assays of GPCR agonist-stimulated growth of cells containing the M3 MAR IC3Δ. Specifically, the plasmids were introduced into the MPY578fc cells described in Pausch et al. (1998).

Figure 1B:
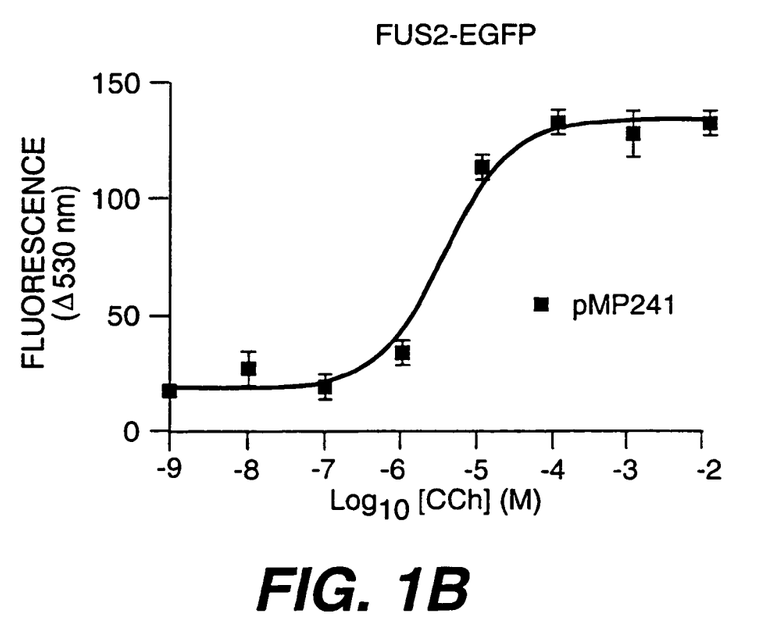
FIG. 1B depicts the results of liquid culture fluorescence induction assays on yeast cells containing the rat M3 MAR IC3Δ and the FUS2-GFP reporter plasmid using the MAR agonist carbachol (CCh). A dose-dependent increase in the expression of the green fluorescent protein is observed in response to CCh activation of the M3 MAR IC3Δ expressed in yeast.

Yeast cells containing the M3 MAR IC3Δ and the FUS2-EGFP reporter plasmid were assayed in liquid culture using the MAR agonist carbachol (CCh). The cells were cultured overnight in 2 ml SC-glucose-ura medium. The cells were washed and diluted 5 fold in SC-glucose-ura-his, pH 6.8 medium containing 5 mM 3-aminotriazole to decrease basal growth rate. Samples of the cell suspension (180 μl) were dispensed to wells of sterile 96 well microtiter dishes containing 20 μl of serially-diluted samples ($10^{-1}$–$10^{-8}$ M) of CCh. The plates were incubated at 30° C. for 6 hours with agitation (600 rpm). Stimulation of the FUS2-EGFP reporter gene expression was monitored by recording increases in emission at 530 nm after excitation with 480 nm light using a fluorescence microplate reader. Assays were conducted in duplicate and measurements obtained during the logarithmic phase of yeast cell growth. Fluorescence emission measurements were analyzed using GraphPad Prism and were presented as the mean±SEM and were plotted vs. agonist concentration. As shown in FIG. 1B, the yeast cells containing the M3 MAR IC3Δ produced a dose dependent increase in florescence emission, consistent with increased expression of the EGFP from the agonist inducible FUS2-GFP reporter gene construct. The EC50 for CCh stimulation of fluorescence emission is 4 μM, identical to values obtained in the growth assay.

Thus, deletion of a portion of the IC3 of the rat M3 MAR has produced a functional GPCR when expressed in yeast, suggesting that modification of internal domains may be a generalizable method for improving the function of heterologous GPCRs expressed in yeast.

EXAMPLE 2

Functional Expression of a Mutated *D. melanogaster* Muscarinic Acetylcholine Receptor in Yeast Agonist of the G protein-coupled insect muscarinic acetylcholine receptors (MARs) possess substantial insecticidal and miticidal activity. M. R. Dick et al. (1997). These observations suggest that development of a yeast-based high throughput screen (HTS) for agonists active at insect MARs may be useful in identifying lead compounds that might be developed into insecticides with novel mode of action. Preliminary experiments indicate that the wild type *D. melanogaster* MAR (DMAR), an insect G protein-coupled receptors (GPCRs), is non-functional in yeast. Thus, an effort to develop a method for improving the function of the DMAR in yeast was mounted, via replacement of the DMAR IC3 with the functional IC3 from the M3 MAR IC3Δ.

In insect cells, the DMAR interacts with the heterotrimeric Gq protein leading to an increase in intracellular calcium in response to muscarinic agonists. One potential explanation for the inactivity of the DMAR in yeast is an inability to efficiently couple to the yeast heterotrimeric G protein. Thus, to devise a method to improve the DMAR function in yeast, selected mutations in the GPCRs that serve to improve functional expression and coupling to the heterotrimeric G protein were examined.

In order to construct the IC3 replacement, PCR fragments encoding three domains were prepared by standard means. Fragment 1 consisted of the amino terminal coding portion of the *Drosophila* MAR up to an AgeI site within the 5th TMD, amplified by PCR using oligonucleotides (AAA AGATCT AAA ATG TACGGAAACCAGACGAAC) (SEQ ID NO: 7) and (CCA GTA GAG GAA GCACATGATGGTC AGGCCT AAG TAG AAG GCG GCC AGT GC) (SEQ ID NO: 8). The second fragment of the DMAR was composed of carboxy terminal coding sequences starting with a PmlI site in the 6th TMD, amplified by PCR using oligonucleotides (TTCATCATCACGTGGACTCCGTACAACATC) (SEQ ID NO: 9) and (AAA CTCGAG TTATCTAATTGTA-GACGCGGC) (SEQ ID NO: 10). The M3 MAR IC3Δ domain was amplified as an AgeI-PmlI fragment with coding sequence in frame with fragments 1 and 2, described in Example 1. These fragments were assembled in plasmid p426GPD to place the mutated DMAR under control of the GPD promoter. The wild type DMAR was cloned into the expression vector, pMP3, described in U.S. Pat. No. 5,691,188. Using a conventional lithium acetate transformation procedure, the resulting plasmids were introduced into yeast cells useful for performing assays of GPCR agonist-stimulated growth, such as those described in U.S. Pat. No. 5,691,188, including, specifically, the MPY578fc cells described in Pausch et al. (1998).

Figure 2:
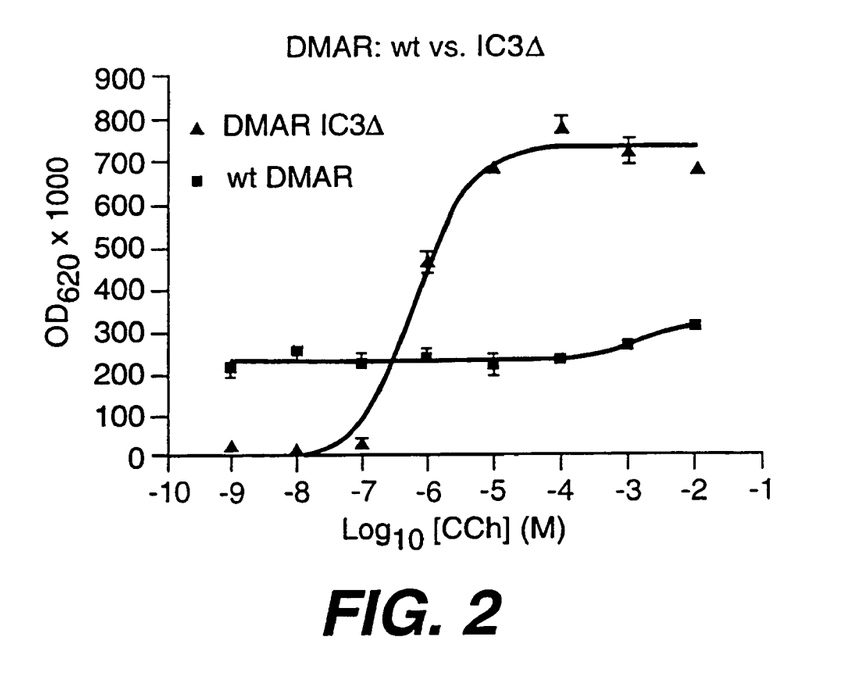
FIG. 2 depicts the results of liquid culture assays on yeast cells containing the *Drosophila* muscarinic acetylcholine receptor using the MAR agonist carbachol (CCh). Yeast cells containing a mutated *Drosophila* MAR containing the M3 MAR IC3Δ produced an agonist-dependent growth response while the wild type *Drosophila* MAR lacked an agonist-dependent yeast cell growth response.

Yeast cells containing the DMAR and the plasmid containing the wild type DMAR were assayed in liquid culture using the MAR agonist carbachol (CCh). The cells were cultured overnight in 2 ml SC-glucose-ura medium. The cells were diluted 500 fold in SC-glucose-ura-his, pH 6.8, medium containing 5 mM 3-aminotriazole to decrease basal growth rate. Samples of the cell suspension (180 μl) were dispensed to wells of sterile 96 well microtiter dishes containing 20 μl of serially-diluted samples ($10^{-1}$–$10^{-8}$ M) of the muscarinic receptor agonists. The plates were incubated at 30° C. for 18 hours with agitation (600 rpm). Growth was monitored by recording increases in OD620 using a microplate reader. Assays were conducted in duplicate and growth rate measurements obtained during the logarithmic phase of yeast cell growth. Optical density measurements were analyzed using GraphPad Prism and are presented as the mean±SEM and were plotted vs. agonist concentration. As shown in FIG. 2, the yeast cells containing the mutated DMAR, i.e., the M3 MAR IC3Δ, produced an agonist-dependent growth response, demonstrating that the DMAR-M3 MAR IC3 Δ is functional. The wild type DMAR is non-functional, as indicated by the lack of agonist-dependent yeast cell growth.

Thus, replacing IC3 of the DMAR with the functional deleted IC3 from the rat M3 MAR produces a functional chimeric GPCR when expressed in yeast, indicating that this method of replacing internal domains may be a generalizable method for improving the functional expression of heterologous GPCRs in cell-based assays, such as yeast assays.

EXAMPLE 3

Functional Expression of a Mutated Rat Cholecystokinin CCKB Receptor in Yeast

As shown in Examples 1 and 2, deletion of portion of the IC3 of mammalian MARs, in particular the rat M3 MAR, is correlated with improved functional expression in mammalian and yeast cells with retention of full ability to couple to the heterotrimeric G protein. In order to test the possibility that this IC3Δ mutation would also improve functional expression of other GPCRs in yeast, the DNA sequences encoding the rat wild type and IC3Δ cholecystokinin CCKB receptor were amplified by PCR and cloned into proximity to the glycerol-phosphate dehydrogenase promoter in yeast expression plasmid, p426GPD, by standard methods. The wild type CCKBR was amplified by PCR using oligonucleotides (ACTTAGATCAAAAAATGGAGCGCT-CAAGCTGAACCG) (SEQ ID NO: 11) and (TCCCGTC-GACTCAGCCAGGCCCCAGTGTGCTG) (SEQ ID NO: 12). The IC3Δ cholecystokinin CCKB receptor was prepared by fusing two overlapping fragments. Fragment 1 contained amino terminal coding sequences including 22 amino acids proximal to the 5th TMD, amplified by PCR using oligonucleotides (ACTTAGATCAAAAAATG-GAGCGCTCAAGCTGAACCG) (SEQ ID NO: 11) and (CGAGGGCCAGGGACTGGCCCCGGC-CGGGCCCGGCTTTGGGTCTCG) (SEQ ID NO: 13). Fragment 2 contained carboxy terminal coding sequences including 22 amino acids proximal to the 6th TMD, amplified by PCR using oligonucleotides (TCCCGTCGACT-CAGCCAGGCCCCAGTGTGCTG) (SEQ ID NO: 12) and (CGAGACCCAAAGCCGGGCCCGGC-CGGGGCCCAGTCCCTGGCCCTCG) (SEQ ID NO: 14). The two fragments were fused by amplification by PCR using oligos at 5' and 3' ends of the full length CCKB receptor. Using a conventional lithium acetate transformation procedure, the resulting plasmids were introduced into yeast cells useful for performing assays of GPCR agonist-stimulated growth, such as those described in U.S. Pat. No. 5,691,188, including, specifically, the MPY578fc cells described in Pausch et al. (1998).

Figure 3A:
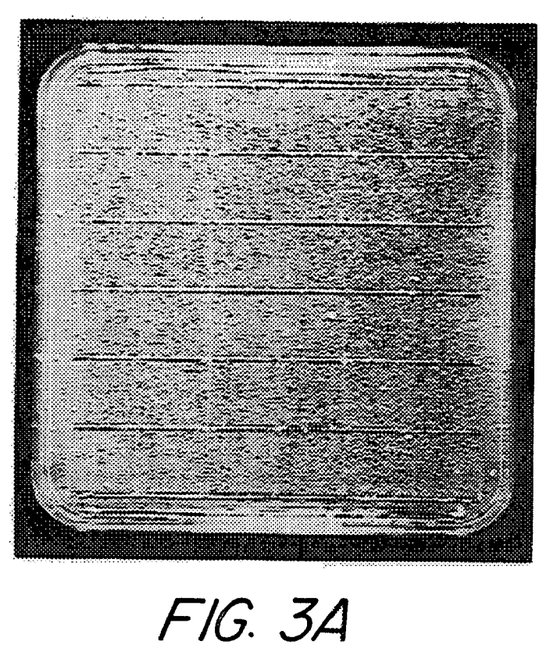
FIG. 3A shows a robust growth response of yeast cells containing the IC3Δ cholecystokinin CCKB receptor.
Figure 3B:
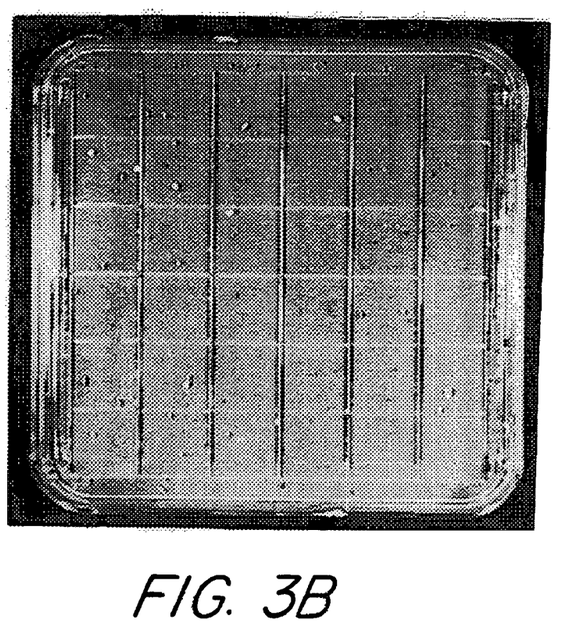
FIG. 3B shows only limited growth by yeast cells containing the wild type CCKB receptor, indicating that the deletion of a portion of the third intracellular loop of the CCKB receptor improves its function in yeast.

Yeast strains containing wild type and IC3Δ cholecystokinin CCKB receptor were grown overnight in 2 ml synthetic complete liquid medium containing glucose (2%) and lacking uracil (SCD-ura) medium. In this agar-based plate bioassay, molten (50° C.) SCD-ura-his agar medium (35 ml, adjusted to pH 6.8 by addition of concentrated KOH or NH$_4$OH prior to autoclaving) containing 0.5 mM AT (3-aminotriazole) was inoculated with the overnight culture (2×10$^4$ cells/ml) and poured into square (9×9 cm) petri plates. Solutions of CCK agonists in DMSO (1 mM, 10 μl) were applied to the surface of the solidified agar (Upper left: CCK8S; upper right, CCK8US; lower left, CCK5; lower right, CCK4). Compounds applied to the surface of the plate diffused radially from the site of application and bound to CCKB receptors expressed on the surface of cells embedded in the agar, resulting in induction of FUS1-HIS3 expression. The responding cells formed a dense growth zone readily detectable over the limited growth of cells observed in response to basal FUS1-HIS3 expression. Plates were incubated at 30° C. for 3 days (FIG. 3). FIG. 3A demonstrates the robust growth response of yeast cells containing the IC3Δ cholecystokinin CCKB receptor, while FIG. 3B shows only limited growth by yeast cells containing the wild type CCKB receptor, indicating that the deletion of portion of the third intracellular loop of the CCKB receptor improves its function in yeast.

EXAMPLE 4

Functional Expression of a Mutated Rat Somatostatin Receptor (SSTR) in Yeast

The third intracellular loop participates in many GPCR functions, including G protein coupling, desensitization and interaction with diverse modifying proteins.

Somatostatin receptors are encoded in five subtypes, labeled SSTR1-5. Several amino acids are found in the third intracellular loop of the SSTR3 subtype, but not in the equivalent region of SSTR2 subtype. Since SSTR2 functions efficiently in yeast, deletion of those amino acids from IC3 may impart this functional efficiency upon SSTR3. Thus, 8 amino acids, Gln-Trp-Val-Gln-Ala-Pro-Ala-Cys (SEQ ID NO: 15), were deleted from the third intracellular loop of the rSSTR3 cDNA, enabling more efficient receptor signaling in yeast.

Rat SSTR3 sequences were amplified by PCR using oligonucleotides containing 5' BglII and 3' XhoI sites. The resulting PCR product of approximately 1.3 kb was digested with BglII and XhoI, purified and inserted between the BamHI and XhoI sites in p426GPD to generate the plasmid p426GPD-rSSTR3. Recombinant plasmids were confirmed by restriction endonuclease digestion and DNA sequencing.

Standard PCR reactions were used to amplify the rSSTR3 cDNA to yield two PCR fragments that have 36 bp overlap as follows. PCR insert A of approximate size 750 bp was generated using the 5' Bgl oligonucleotide (AAAAAGATCT AAAATGGCCA CTGTTACCTA T) (SEQ ID NO: 16) and the 3' oligonucleotide CTCAGAGCGG CGTCGCCGCT GACACGAGGG CGCCCG (SEQ ID NO: 17). PCR insert B of approximate size 530 bp was generated using the 5' oligonucleotide GCGCCCTCGT GTCAGCGGCG ACGC-CGCTCT GAG (SEQ ID NO: 18) and the 3' XhoI oligonucleotide (AAAACTCGAG TTACAGATGG CTCAGT-GTGC T) (SEQ ID NO: 19). PCR fragments A and B were gel purified, annealed and amplified by PCR using the flanking 5' BglII and 3' XhoI oligonucleotides to yield the ~1.3 kb rSSTR3ΔIC3 PCR product. Following purification and digestion with BglII-XhoI, the rSST3ΔIC3 insert was ligated into BamHI-XhoI sites of p426GPD to generate the plasmid p426GPD-rSSTR3ΔIC3. Restriction mapping and DNA sequencing confirmed correct reading frame and sequence.

Figure 4A:
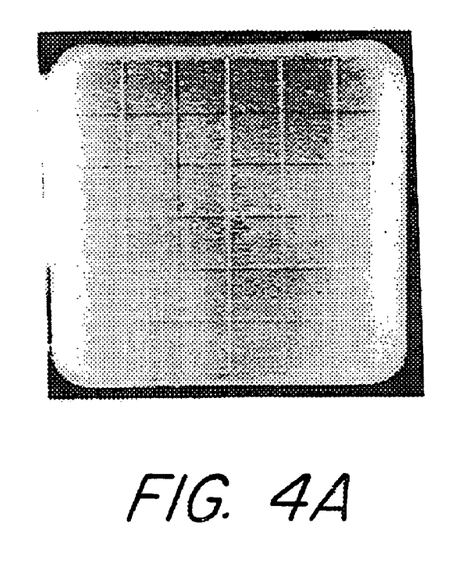
FIG. 4A demonstrates that yeast cells containing p426GPD-rSSTR3 show a weak response to somatostatin (S-14).
Figure 4B:
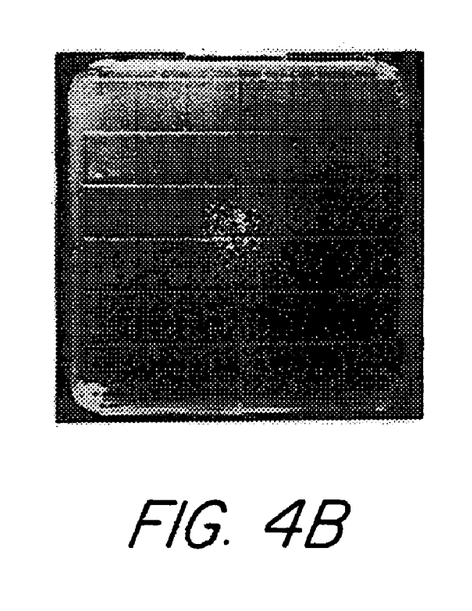
FIG. 4B demonstrates a much stronger response by yeast cells containing p426GPD-rSSTR3ΔIC3 assayed under similar conditions.

Yeast cells of the type useful for expression of GPCRs, described in U.S. Pat. No. 5,691,188, were transformed with p426GPD-rSSTR3 and p426GPD-rSSTR3ΔIC3, using standard procedures. The cells (i.e., the LY296 cells, described in Price et al. (1995)) were assayed using the agar-based bioassay format described in Example 3. Samples (10 μl) of Somatostatin (S-14, 1 mM) were applied to the surface of the selective agar medium containing the yeast cells expressing the SSTR3. The plates were incubated for 3 days at 30° C. Yeast cells transformed with p426GPD-rSSTR3 along with pLP82 (containing a Gpal/Gαi2 chimeric G-protein expression plasmid) showed a weak growth response to S-14 (FIG. 4A), whereas a much stronger response was observed when p426GPD-rSSTR3ΔIC3 was assayed under similar conditions (FIG. 4B). These results indicate that deletion of a portion of the IC3 improves the function of the SSTR3 in yeast.

EXAMPLE 5

An IC3 Deleted Human Alpha2A Adrenergic Receptor

As shown in Examples 1–4, deletion of portion of the IC3 of mammalian GPCRs is correlated with improved functional expression in mammalian and yeast cells with retention of full ability to couple to the heterotrimeric G protein. The mutated MARs, CCKBR, and SSTR3 retain all external loops. Transmembrane domains and internal domains other than the IC3 are unchanged. The IC3, found between 5th and 6th membrane spanning helices, was the only domain modified. The bulk of this domain was deleted leaving only 22 amino acids proximal to both the 5th and 6th transmembrane helices. Thus, IC3 of the GPCRs containing the IC3 deletion (IC3Δ) is 44 amino acids in length. The improvement in functional expression may be due to elimination of domains known to interact with cellular desensitization mechanisms, allowing more functional MAR to be retained at the cell surface.

In order to test the possibility that other IC3Δ mutations would also improve functional expression of other GPCRs in yeast, DNA sequences encoding an IC3Δ human alpha2A adrenergic receptor were amplified by PCR and cloned into proximity to the glycerol-phosphate dehydrogenase promoter in yeast expression plasmid, p426GPD, by standard methods. The IC3Δ human alpha2A adrenergic receptor was prepared by fusing two overlapping fragments. Fragment 1 contained amino terminal coding sequences including 39 amino acids proximal to the 5th TMD, amplified by PCR using oligonucleotides (GGCCAGGATCCAAAAATGGGCTCCCTGCAGCCGGACGC) (SEQ ID NO: 20) and (CGGGCCCCGCGGGCGCTCGGGGCCCAGACCGTTGGGC) (SEQ ID NO: 21). Fragment 2 contained carboxy terminal coding sequences including 41 amino acids proximal to the 6th TMD, amplified by PCR using oligonucleotides (CGGGCGACAGCCTGCCGCGGC) (SEQ ID NO: 22) and (AGCGGTCGACTCACACGATCCGCTTCCTGTCCCC) (SEQ ID NO: 23). The two fragments were fused by amplification by PCR using oligos at 5' and 3' ends of the full length alpha2A adrenergic receptor. Using a conventional lithium acetate transformation procedure, the resulting plasmids were introduced into yeast cells useful for performing assays of GPCR agonist-stimulated growth, such as those described in U.S. Pat. No. 5,691,188, including, specifically, the MPY578fc cells described in Pausch et al. (1998).

Yeast cells containing the wild type IC3Δ human alpha2A adrenergic receptor were assayed in liquid culture using the alpha adrenergic receptor full agonist UK14304 (RBI) and partial agonist clonidine. The cells were cultured overnight in 2 ml SC-glucose-ura medium. The cells were diluted 500 fold in SC-glucose-ura-his, pH 6.8 medium. Samples of the cell suspension (180 μl) were dispensed to wells of sterile 96 well microtiter dishes containing 20 μl of serially-diluted samples of the adrenergic receptor agonist, UK14304 ($10^{-3}$–$10^{-10}$ M). The plates were incubated at 30° C. for 18 hours with agitation (600 rpm). Growth was monitored by recording increases in OD620 using a microplate reader. Assays were conducted in duplicate and growth rate measurements obtained during the logarithmic phase of yeast cell growth. Optical density measurements were analyzed using GraphPad Prism and are presented as the mean±SEM and were plotted vs. agonist concentration.

Figure 5:
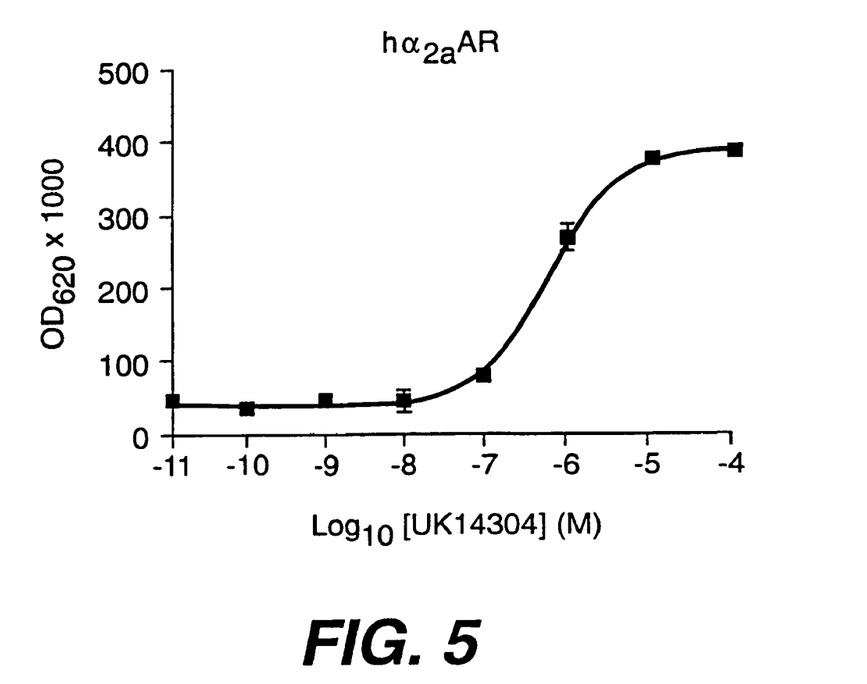
FIG. 5 depicts the results of liquid culture assays on yeast cells containing wild type IC3Δ human alpha2A adrenergic receptor using the alpha adrenergic receptor full agonist UK14304. Yeast cells containing the wild type and IC3Δ human alpha 2A adrenergic receptor produced a dose-dependent growth response, indicating that the IC3 deletion is functional.

The yeast cells containing the wild type IC3Δ human alpha 2A adrenergic receptor produced a dose-dependent growth response, indicating that this IC3 deletion is functional (FIG. 5).

EXAMPLE 6

Truncation of the Rat Neurotensin NT1 Receptor Causes an Increase in Agonist Sensitivity In examples 1–4, modification of the third intracellular loop leads to improvement in functional expression of a variety of heterologous GPCRs expressed in yeast. Agonist induced desensitization of the GPCRs is also mediated in part by GPCR internal domains other than the third intracellular loop, such as the intracellular carboxy-terminal tail.

Elimination of the carboxy terminal domains from GPCRs has been shown to improve functional expression in yeast and mammalian cells. Truncation of the carboxy terminal tail of the G protein-coupled alpha mating pheromone receptor expressed in α-mating type yeast cells causes supersensitivity to the presence of mating pheromone (Reneke et al. (1988); Konopka et al (1988)). Consistent with these observations, a mutated rat neurotensin NT1 receptor (rNTR1) lacking its carboxy terminal tail is resistant to agonist-induced internalization when expressed in mammalian cells (Hermans et al. (1996)).

To test whether carboxy-terminal truncation improves the functional response of a heterologous GPCR expressed in yeast, the rat NTR1 was modified by deleting the 52 amino acids that constitute the carboxy terminal tail, leaving a shortened receptor 372 amino acids in length. The coding sequences of the wild type and truncated neurotensin NT1 receptor (rNTR1 C-term Δ), were amplified by PCR using a 5' oligonucleotide primer that specified a common amino-terminal coding sequence (AGTCAGATCTAAGCTT AAAA ATG CAC CTC AAC AGC TCC) (SEQ ID NO: 24) and separate oligos that define the wild type (AGTC AGATCT CTA GTA CAG GGTCTCCC) (SEQ ID NO: 25) and truncated carboxy termini (AGAG AGATCT TTAGCGCCACCCAGGACAAAGGC) (SEQ ID NO: 26). These fragments were cloned into proximity of the PGK promoter in the yeast expression vector pPGK by standard methods (Y-S. Kang et al. (1990)). Using a conventional lithium acetate transformation procedure, the resulting plasmids were introduced into yeast cells of the kind described in U.S. Pat. No. 5,691,188 that are useful for performing assays of GPCR agonist-stimulated growth, including, specifically, the MPY578fc cells described in Pausch et al. (1998).

Figure 6:
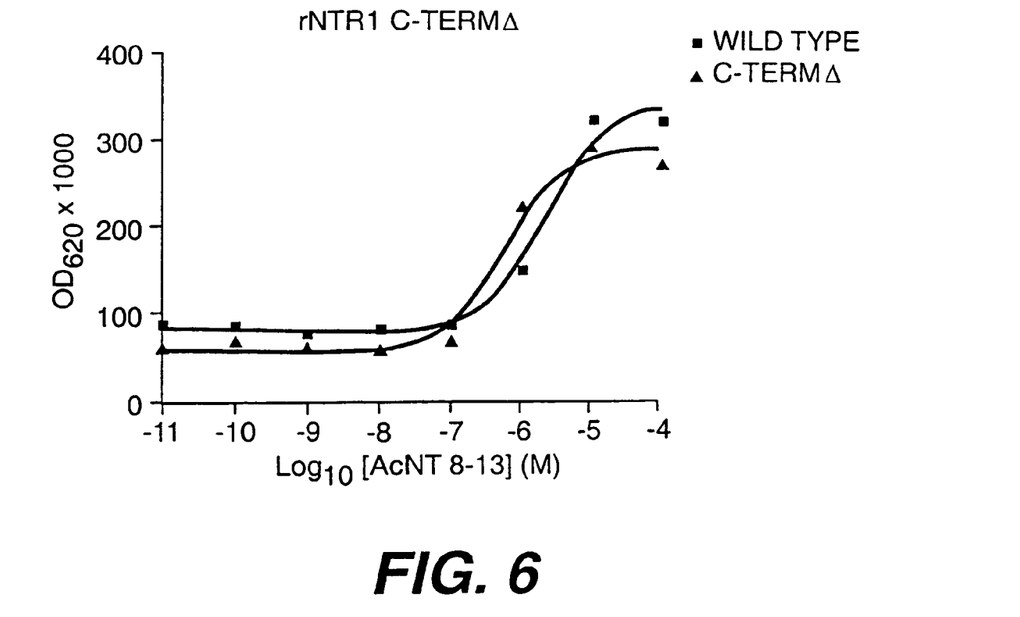
FIG. 6 depicts the results of liquid culture assays on yeast cells containing wildtype and carboxy terminally truncated rat NT1-neurotensin receptors using the neurotensin receptor agonist AcNT8-13. Truncation of the rat NT1-neurotensin receptor produces an agonist-dependent growth response that is more sensitive than that observed with the wildtype receptor.

Yeast cells containing the NTR1s were assayed in liquid culture using the NT receptor agonist acetyl neurotensin 8-13 (AcNt8-13). The cells were cultured overnight in 2 ml SC-glucose-ura medium. The cells were diluted 500 fold in SC-glucose-ura-his, pH 6.8 medium containing 2 mM 3-aminotriazole to decrease basal growth rate. Samples of the cell suspension (180 μl) were dispensed to wells of sterile 96 well microtiter dishes containing 20 μl of serially-diluted samples ($10^{-3}$–$10^{-10}$ M) of AcNT8-13. The plates were incubated at 30° C. for 18 hours with agitation (600 rpm). Growth was monitored by recording increases in $OD_{620}$ using a microplate reader. Growth rate measurements were obtained during the logarithmic phase of yeast cell growth. Optical density measurements were analyzed using GraphPad Prism and are presented as the mean±SEM and were plotted against agonist concentration. As shown in FIG. 6, the yeast cells containing the NTR1s produced an agonist-dependent growth response demonstrating that both the wild type and carboxy terminally truncated NTR1s were functional. The growth response of the rNTR1 C-term Δ containing cells was dose-dependent giving an EC50 for AcNT8-13 equal to 520 nM. This value is five fold lower than observed for cells expressing the wild type NTR1 (2.1 μM). The carboxy terminal deletion has produced a rNTR1 that responds to a lower concentration of NTR agonist improving the sensitivity of the yeast bioassay.

Thus, deletion of a portion of the carboxy terminal intracellular domain of the rat NTR1 has produced a functional GPCR with increased agonist sensitivity when expressed in yeast, suggesting that modification of this internal domain is a generalizable method for improving the function of heterologous GPCRs expressed in yeast.

EXAMPLE 7

Functional Expression of a Mutated C. elegans Serotonin Receptor in Yeast

Agonists of the G protein-coupled C. elegans serotonin receptor (Ce 5HTR) may possess substantial nematacidal activity. These observations suggest that development of a yeast-based HTS for agonists active at Ce 5HTRs may be useful in identifying lead compounds that might be developed into nematacides with a novel mode of action. Preliminary experiments indicated that the wild type Ce 5HTR was non-functional in yeast. Thus, an effort to develop a method for improving the function of the Ce 5HTR in yeast was mounted, via replacement of the Ce 5HTR IC3 with the functional IC3 from the M3 MAR IC3Δ.

In order to construct the IC3 replacement, PCR fragments encoding three domains were prepared by standard means. Fragment 1 contains the amino terminal-coding portion of the Ce 5HTR to the intracellular interface of the 5th TMD, amplified by PCR using oligonucleotides (AAAA-GATCTAAAATGATCGACGAGACGCTTC) (SEQ ID NO: 27) and (CCGCTTGGTGATCTGACTTCTG-GTTTCTGTCCCAGAGGCCTGTAGGCCAG CCAGCTCTTTGGTACGCTTCTCAGTTTC-CTTATAGATCTTCCAGTACACGC AAATTATTGC) (SEQ ID NO: 28). The second fragment of the Ce 5HTR contains carboxy-terminal coding sequences starting proximal to the intracellular interface of the 6th TMD, amplified by PCR using oligonucleotides (AAAACTCGAGT-CAATAATCGTGAATAAGGCA) (SEQ ID NO: 29) and (GGCCTACAGGCCTCTGGGACAGAAACCA-GAAGTCAGATCACCAAGCGGA AGAGGATGTCGCT-CATCAAGGAGAAGAAGGCCGCCA-GAACGCTAGCAAT TATTACAGGTAC) (SEQ ID NO: 30). The M3 MAR IC3Δ domain was amplified by PCR as described in Example 1.

These fragments were isolated, mixed and amplified by PCR with 5' (AAAAGATCTAAAATGATCGAC-GAGACGCTTC) (SEQ ID NO: 27) and 3' (AAAACTC-GAGTCAATAATCGTGAATAAGGCA) (SEQ ID NO: 29) oligonucleotides. The resulting fragment was digested with appropriate restriction endonucleases and assembled in p426GPD to place the mutated Ce 5HTR under control of the GPD promoter. Using a conventional lithium acetate transformation procedure, the resulting plasmids were introduced into yeast cells useful for performing assays of GPCR agonist-stimulated growth, such as those described in U.S. Pat. No. 5,691,188, including, specifically, the MPY578fc cells described in Pausch et al. 1998.

Figure 7:
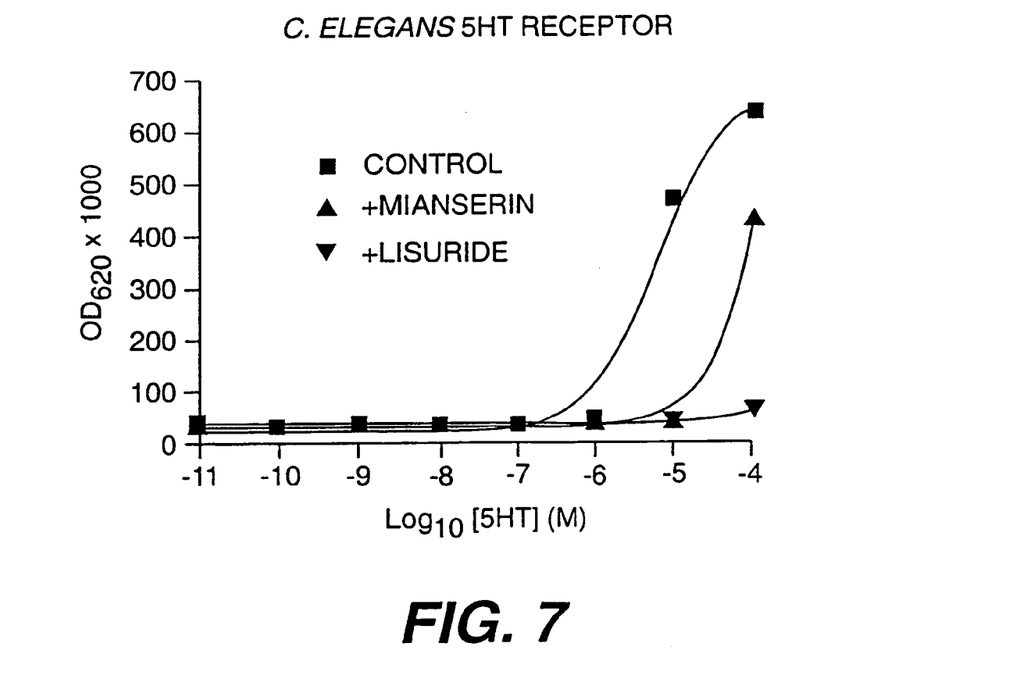
FIG. 7 depicts the results of liquid culture assays on yeast cells containing the *C. elegans* serotonin receptor using serotonin (5HT) to stimulate yeast cells growth. Yeast cells containing a mutated *C. elegans* serotonin receptor containing the M3 MAR IC3Δ produced a 5HT-dependent growth response. The growth response was blocked by addition of the serotonin receptor antagonists lisuride and mianserin.

Yeast cells containing the Ce 5HTR were assayed in liquid culture. The cells were cultured overnight in 2 ml SC-glucose-ura medium. The cells were diluted 500 fold in SC-glucose-ura-his, pH 6.8 medium containing 2 mM 3-aminotriazole to decrease basal growth rate. Samples of the cell suspension (200 μl) were dispensed to wells of sterile 96 well microtiter dishes containing 2.0 μl of serially-diluted samples ($10^{-2}$–$10^{-9}$ M) of serotonin (5HT). In similar reactions, the serotonergic antagonists lisuride and mianserin were added to each well at 10 μM. The plates were incubated at 30° C. for 18 hours with agitation (600 rpm). Growth was monitored by recording increases in OD620 using a microplate reader. Assays were conducted in duplicate and growth rate measurements were obtained during the logarithmic phase of yeast cell growth. Optical density measurements were analyzed using GraphPad Prism and are presented as the mean±SEM, plotted vs. agonist concentration. Ki values were determined using the equation of Cheng and Pruesoff. (Y Cheng et al. (1973)). As shown in FIG. 7, the yeast cells containing the mutated Ce 5HTR containing the M3 MAR IC3Δ produced an agonist-dependent growth response, demonstrating that the Ce 5HTR-M3 MAR IC3Δ is functional. As expected, the serotonergic antagonists lisuride and mianserin blocked the growth inducing effect of serotonin, demonstrating that the Ce 5HTR exhibits the expected pharmacological properties when expressed in yeast.

Thus, replacing IC3 of the Ce 5HTR with the functional deleted IC3 from the rat M3 MAR produces a functional chimeric GPCR when expressed in yeast, indicating that this method of replacing internal domains may be a generalizable method for improving the functional expression of heterologous GPCRs in cell-based assays, such as yeast assays.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The references cited herein are specifically incorporated by reference in their entirety.

REFERENCES

C. Boone et al., "Mutations That Alter the Third Cytoplasmic Loop of the A-Factor Receptor Lead to a Constitutive and Hypersensitive Phenotype," Genetics, *Proc. Nat'l. Acad. Sci. USA.*, 90:9921–9925 (November 1993).

M. G. Caron, "The Guanine Nucleotide Regulatory Protein-Coupled Receptors for Nucelotides, Amino Acids, and Amine Neurotransmitters," *Cell Biology*, 1:159–166 (1989).

Y. Cheng et al., "Relationship between the inhibition constant (Ki) and the concentration of inhibitor which causes 50 percent inhibition (150) of an enzymatic reaction," *Biochem. Pharmacol.*, 22: 3099–3108 (1973).

C. D. Clark et al., "Systematic Mutagenesis of the Yeast Mating Pheromone Receptor Third Intracellular Loop," *J. Biol. Chem.*, 269(12):8831–8841 (1994).

B. R. Conklin and H. R. Bourne, "Structural Elements of G Alpha Subunits that Interact with G Beta Gamma Receptors, and Effectors," *Cell*, 73:631–641 (1993).

M. R. Dick et al., "Muscarinic Agonists as Insecticides and Acaricides," *Pestic. Sci.*, 49:268–276 (1997).

H. G. Dohiman et al., "Model Systems for the Study of Seven-Transmembrane-Segment Receptors," *Ann. Rev. Biochem.*, 60:653–688 (1991).

E. Hermans et al., "Interaction of the COOH-Terminal Domain of the Neurotensin Receptor with a G Protein Does Not Control the Phospholipase C Activation But is Involved in the Agonist Induced Internalization," *Mol. Pharmacol*, 49:365–372 (1996).

Y. S. Kang et al., "Effects of Expression of Mammalian G Alpha and Hybrid Mammalian-Yeast G Alpha Proteins on the Yeast Pheromone Response Signal Transduction Pathway," *Mol. Cell. Biol.*, 10(6):2582–2590 (1990).

J. B. Konopka et al., "The C-Terminus of the *S. cerevisiae* Alpha Pheromone Receptor Mediates an Adaptive Response to Pheromone," *Cell*, 54:609–620 (1988).

M. Krieger et al., "Isolation of Chinese Hamster Cell Mutants Defective in the Receptor-Mediated Endocytosis of Low Density Lipoprotein," *J. Mol. Biol.,* 150(2); 167–84 (August 1981).

J. Lameh et al., "Hm1 Muscarinic Cholinergic Receptor Internalization Requires a Domain in the Third Cytoplasmic Loop," *J. Biol. Chem.,* 267(19):13406–13412 (1992).

S. B. Liggett et al., "Sites in the Third Intracellular Loop of the $\alpha_{2A}$-Adrenergic Receptor Confer Short Term Agonist-Promoted Desensitization," *J. Biol. Chem.,* 267(7):4740–4746 (1992).

O. Moro et al., "Serine- and Threonine-rich Domain Regulates Internalization of Muscarinic Cholinergic Receptors," *J. Biol. Chem.,* 268(10):6862–6865 (1993).

M. H. Pausch et al., "G-Protein-Coupled Receptors in *Saccharomyces Cerevisiae*: High-Throughput Screening Assays for Drug Discovery," *Trends in Biotechnology,* 15:487–494 (1997).

M. H. Pausch et al., "Heterologous G protein-coupled receptors in *Saccharomyces cerevisiae*, Methods for genetic analysis and ligand identification," *Identification and expression of G protein-coupled receptors,* Lynch, K. R., Ed., Wiley-Liss, New York, N.Y., 196–212 (1998).

L. A. Price et al., "Functional coupling of a mammalian somatostatin receptor to the yeast pheromone response pathway," *Mol. Cell. Biol.* 15, 6188–6195, (1995).

J. E. Reneke et al., "The Carboxy Terminal Segment of the Yeast Alpha Factor Receptor Is a Regulatory Domain," *Cell,* 55:221–234 (1988).

A. B. Tobin et al., "Identification of a Novel Receptor Kinase That Phosphorylates A Phospholipase C-linked Muscarinic Receptor," *J. Biol. Chem.,* 271(7):3907–3916 (1996).

A. B. Tobin et al., "Stimulus-Dependent Phosphorylation of G-Protein-Coupled Receptors by Casein Kinase 1$\alpha$," *J. Biol. Chem.,* 272(33):20844–20849 (1997).

H. Tsuga et al., "Internalization and Down-Regulation of Human Muscarinic Acetylcholine Receptor m2 Subtypes," *J. Biol. Chem.,* 273(9):5323–5330 (1996).

J. Wess, "G-Protein-Coupled Receptors: Molecular Mechanisms Involved in Receptor Activation and Selectivity of G-Protein Recognition," FASEB J., 11: 346–354 (1997).

---

We claim:

1. A yeast cell comprising a nucleic acid sequence encoding a mutated, heterologous G protein-coupled receptor, wherein the mutation is a deletion mutation in (1) the $3^{rd}$ intracellular loop resulting in a 44 amino acid third intracellular loop comprising 22 residues proximal to the $5^{th}$ and the $6^{th}$ transmembrane domains or (2) the C-terminus, said mutation improving the function of said heterologous G protein-coupled receptor by causing it to couple more efficiently with a heterotrimeric G protein compared to a wild-type form of the heterologous G protein-coupled receptor, and wherein the mutated G protein-coupled receptor is selected from the group consisting of a muscarinic acetylcholine receptor, a cholecystokinin CCKB receptor, a somatostatin receptor, and a serotonin receptor.

2. The yeast cell according to claim 1, wherein the mutation promotes agonist stimulated growth, and wherein the agonist is a G protein-coupled receptor agonist.

3. The yeast cell according to claim 2, wherein the mutation results in an improved coupling between receptor and a chimeric G protein or failure of the receptor to interact with cell desensitization or sequestration-internalization machinery or proper plasma membrane localization.

4. The yeast cell according to claim 1, wherein the deletion is a point mutation.

5. The yeast cell according to claim 1, wherein the G protein-coupled receptor is selected from the group consisting of a muscarinic acetylcholine receptor and a cholecystokinin CCKB receptor.

6. The yeast cell according to claim 1, wherein the muscarinic acetylcholine receptor is a rat M3 muscarinic acetylcholine receptor or a D. melanogaster muscarinic acetylcholine receptor.

7. A method for screening compounds capable of binding to G protein-coupled receptors comprising:
(a) subjecting the yeast cell according to claim 1 to a test compound; and
(b) measuring the effect of the test compounds on cell growth.

8. A yeast cell comprising a heterologous G protein-coupled receptor, wherein the G protein-coupled receptor has a deletion in the $3^{rd}$ intracellular loop resulting in a 44 amino acid third intracellular loop comprising 22 residues proximal to the $5^{th}$ and the $6^{th}$ transmembrane domains, said deletion improving the function of said heterologous G protein-coupled receptor by causing it to couple more efficiently with a heterotrimeric G protein as compared to a wild-type form of the heterologous G protein-coupled receptor.

9. The yeast cell according to claim 8, wherein the deletion promotes agonist stimulated growth, and wherein the agonist is a G protein-coupled receptor agonist.

10. The yeast cell according to claim 9, wherein the deletion results in improved coupling between the heterologous G protein-coupled receptor and a heterotrimeric G protein or failure of the heterologous G protein-coupled receptor to interact with cell desensitization or sequestration-internalization machinery or proper plasma membrane localization.

11. A method for screening compounds capable of binding to G protein-coupled receptors comprising:
(a) subjecting the yeast cell according to claim 8 to a test compound; and
(b) measuring the effect of the test compound on yeast cell growth.

* * * * *